US012616730B2

(12) United States Patent
Park

(10) Patent No.: US 12,616,730 B2
(45) Date of Patent: *May 5, 2026

(54) TOPICAL COMPOSITION COMPRISING AN EXTRACT OF COMBINED HERBS COMPRISING LONGANAE ARILLUS FOR THE TREATMENT OR ALLEVIATION OF SKIN ULCER AND THE USE THEREOF

(71) Applicants: MEDIHELPLINE CO., LTD, Seoul (KR); Ok Nam Park, Seoul (KR)

(72) Inventor: Ok Nam Park, Seoul (KR)

(73) Assignees: MEDIHELPLINE CO., LTD, Seoul (KR); Ok Nam Park, Seoul (KR)

( * ) Notice: Subject to any disclaimer, the term of this patent is extended or adjusted under 35 U.S.C. 154(b) by 579 days.

This patent is subject to a terminal disclaimer.

(21) Appl. No.: 17/911,282

(22) PCT Filed: Mar. 10, 2021

(86) PCT No.: PCT/KR2021/002946

§ 371 (c)(1),
(2) Date: Sep. 13, 2022

(87) PCT Pub. No.: WO2021/182864

PCT Pub. Date: Sep. 16, 2021

(65) Prior Publication Data

US 2023/0127213 A1  Apr. 27, 2023

(30) Foreign Application Priority Data

Mar. 13, 2020  (KR) ........................ 10-2020-0031481
Feb. 19, 2021  (KR) ........................ 10-2021-0022674

(51) Int. Cl.
| | |
|---|---|
| *A61K 36/69* | (2006.01) |
| *A61K 8/9789* | (2017.01) |
| *A61K 9/00* | (2006.01) |
| *A61K 36/236* | (2006.01) |
| *A61K 36/77* | (2006.01) |
| *A61P 17/02* | (2006.01) |
| *A61Q 19/00* | (2006.01) |

(52) U.S. Cl.
CPC ............ *A61K 36/69* (2013.01); *A61K 8/9789* (2017.08); *A61K 9/0014* (2013.01); *A61K 36/236* (2013.01); *A61K 36/77* (2013.01); *A61P 17/02* (2018.01); *A61Q 19/00* (2013.01); *A61K 2236/331* (2013.01); *A61K 2236/333* (2013.01); *A61K 2236/35* (2013.01); *A61K 2800/5922* (2013.01); *A61K 2800/805* (2013.01)

(58) Field of Classification Search
CPC .... A61K 36/69; A61K 8/9789; A61K 9/0014; A61K 36/236; A61K 36/77; A61K 2236/331; A61K 2236/333; A61K 2236/35; A61K 2800/5922; A61K 2800/805; A61K 9/06; A61K 9/08; A61K 36/232; A61K 47/10; A61K 47/14; A61K 47/38; A61K 47/42; A61P 17/02; A61Q 19/00

See application file for complete search history.

(56) References Cited

U.S. PATENT DOCUMENTS

| | | | |
|---|---|---|---|
| 11,207,367 B2 | 12/2021 | Yang et al. | |
| 2011/0318435 A1 | 12/2011 | Yang et al. | |
| 2020/0384056 A1* | 12/2020 | Yang ..................... | A61K 36/346 |
| 2023/0100173 A1* | 3/2023 | Park ........................ | A61P 29/00 424/769 |
| 2023/0103514 A1* | 4/2023 | Park ..................... | A61K 36/232 424/725 |
| 2023/0107274 A1* | 4/2023 | Park ........................ | A61P 19/02 424/773 |

FOREIGN PATENT DOCUMENTS

| | | | | |
|---|---|---|---|---|
| CN | 1660386 A | 8/2005 | | |
| CN | 1762466 A | 4/2006 | | |
| CN | 101244131 A | 8/2008 | | |
| CN | 100556425 C | 11/2009 | | |
| CN | 102014940 A | 4/2011 | | |
| CN | 102380052 A | 3/2012 | | |
| CN | 102380053 A | 3/2012 | | |
| CN | 102614477 A | 8/2012 | | |
| CN | 102362919 B | * 2/2013 | | |
| CN | 103251754 A | 8/2013 | | |
| CN | 110381972 A | 10/2019 | | |
| KR | 10-2010-0018174 A | 2/2010 | | |
| KR | 10-2018-0069756 A | 6/2018 | | |
| KR | 10-1867530 B1 | 6/2018 | | |
| KR | 20180069528 A | 6/2018 | | |
| KR | 10-2019-0100880 A | 8/2019 | | |
| TW | I323177 B | * 4/2010 | .......... | A61K 9/4825 |
| WO | 2011126295 A2 | 10/2011 | | |

(Continued)

OTHER PUBLICATIONS

TW-I323177-B, Translation, 2010, 7 pages. (Year: 2010).*

(Continued)

*Primary Examiner* — Aaron J Kosar
*Assistant Examiner* — Jennifer Lynn Cain
(74) *Attorney, Agent, or Firm* — Bridgeway IP Law Group, PLLC; Sang Ho Lee; Hyun Woo Shin

(57) ABSTRACT

The present invention is related to a topical pharmaceutical composition and cosmetic composition comprising a combined herb extract of Longanae Arillus, Ligustici Tenuissimi Rhizomaand Polygalae radix as an active ingredient to treat and alleviate skin ulcer.

4 Claims, 4 Drawing Sheets

Specification includes a Sequence Listing.

(56) References Cited

FOREIGN PATENT DOCUMENTS

| WO | 2012096463 A2 | 7/2012 |
| WO | 2017/023104 A1 | 2/2017 |

OTHER PUBLICATIONS

CN-102362919-B, translation, 16 pages (Year: 2013).*

Li et al., Characteristics and Clinical Managements of Chronic Skin Ulcers Based on Traditional Chinese Medicine, 2012, Evid Based Complement Alternat Med, 930192. < https://doi.org/10.1155/2012/930192>. (Year: 2012).*

Mingsan Miao et al., "Effect of topical application of two Polygala tenuifolia species decoction on guinea pig skin". Tropical Journal of Pharmaceutical Research, 16(1): 75-81 (Jan. 2017).

Liu Weizhong, "Polygala is effective in treating carbuncle", WeDoctor Holdings, Hangzhou WeDoctor Health Technology Co., Ltd., China (Aug. 26, 2017).

Zhou Quili et al., "Longan Arillus", The Basic Research And Clinical Of Modern Chinese Medicine, p. 327, Tianjing Science & Technology Translation & Publishing Corp., China (Jun. 1, 2012).

Bae, Nayoung et al., "The neuroprotective effect of modified Yeoldahanso-tang via autophagy enhancement in models of Parkinson's disease", Journal of Ethnopharmacology, 2011, vol. 134, No. 2, pp. 313-322.

Jingden, Baigalmaa et al., "Authentication of the oriental medicinal plant ligusticum tennuissimum (Nakai) Kitagawa (Korean Go-Bon) by multiplex pcr", Planta Medica, 2009, vol. 79, No. 6, pp. 648-651.

"Chapters 5, 6, 14" In: John K. Chen, Tina T. Chen: "Chinese Medical Herbology and Pharmacology", Art of Medicine Press, 2004.

* cited by examiner

[Fig. 1]
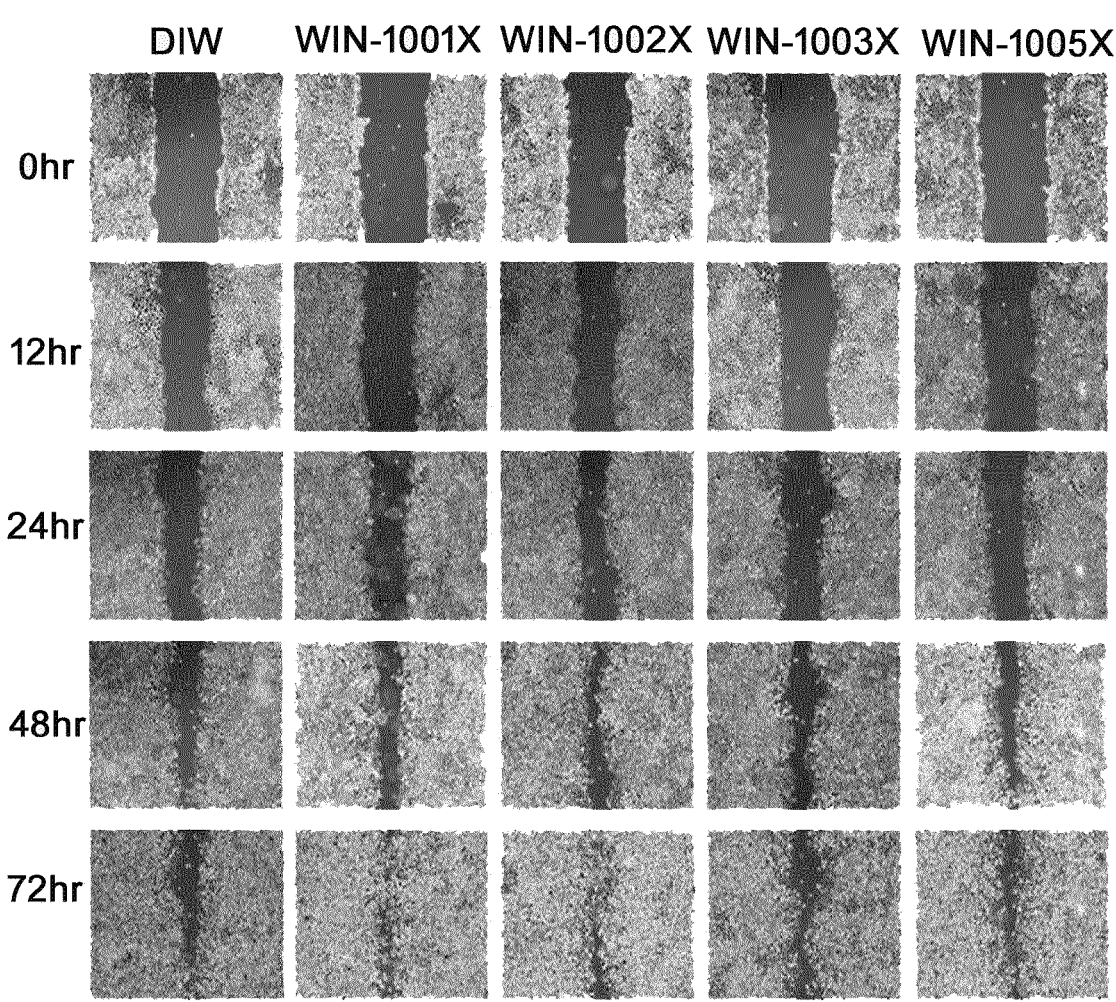

[Fig. 2]
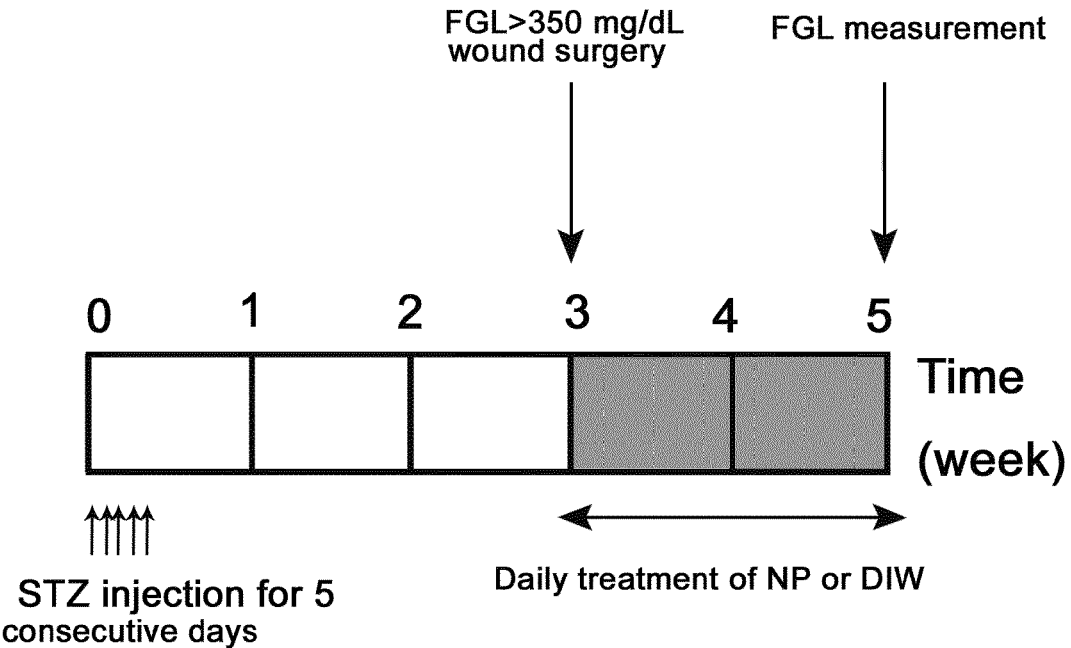

[Fig. 3]
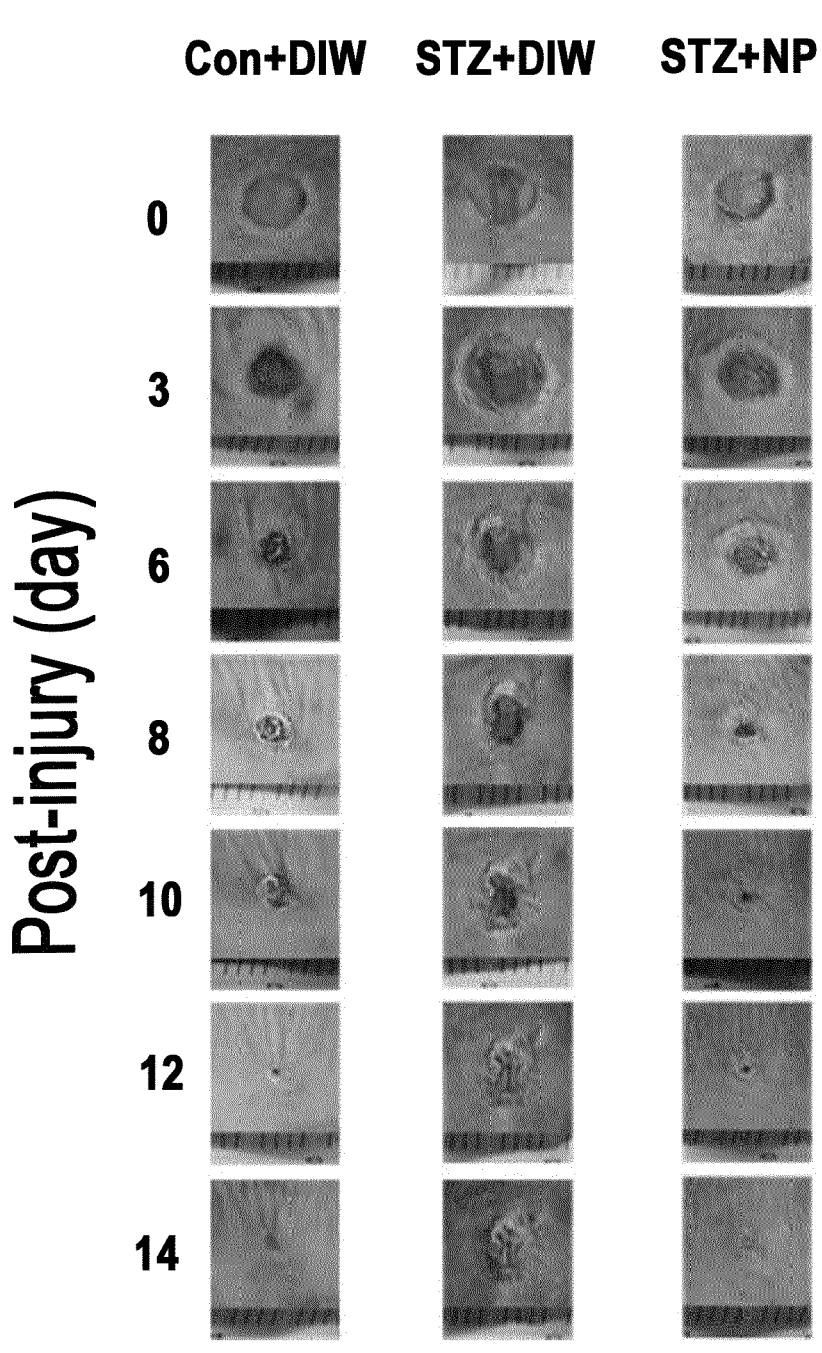

[Fig. 4]
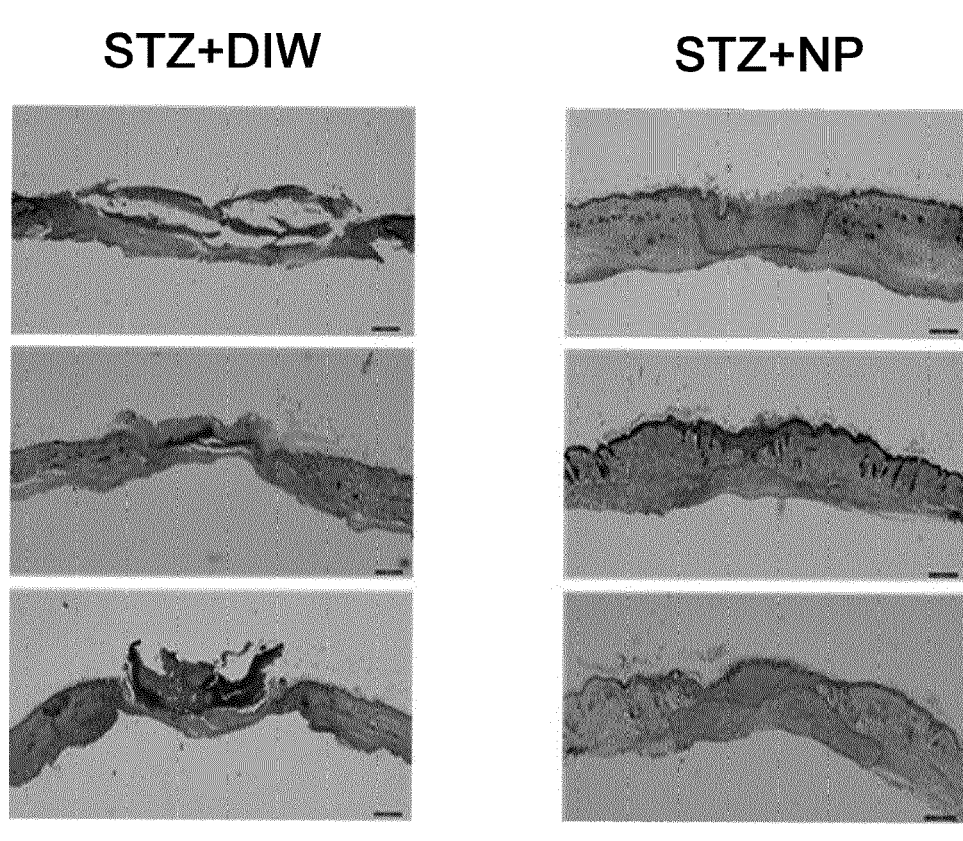

TOPICAL COMPOSITION COMPRISING AN EXTRACT OF COMBINED HERBS COMPRISING LONGANAE ARILLUS FOR THE TREATMENT OR ALLEVIATION OF SKIN ULCER AND THE USE THEREOF

TECHNICAL FIELD

The present invention relates to a topical composition comprising the extract of combined herbs comprising Longanae Arillus for the treatment or alleviation of skin ulcer and the use thereof.

BACKGROUND ART

Skin wound is caused by trauma, bruises, and tear, and wound healing is the process of repairing damaged tissue for the integrity of the skin (Pazyar N, Yaghoobi R, Rafiee E. Mehrabian A, Feily A (2014) Skin Wound Healing and Phytomedicine: A Review. *Skin Pharmacol Physiol.* 27: pp. 303-310.).

Wound healing occurs in four stages of sequential and continuous process: hemostasis, inflammation, proliferation, and remodeling (Demidova-Rice T N, Hamblin M R. Herman I M (2012) Acute and Impaired Wound Healing: Pathophysiology and Current Methods for Drug Delivery, Part 1: Normal and Chronic Wounds: Biology, Causes, and Approaches to Care. *Advances in Skin & Wound Care.* 25:304-314).

This process is very complex but sophisticated through efficient interaction between various cells, proteins, and cytokines, and chronic wounds are formed if the wound healing process is not carried out properly due to various causes.

For example, chronic wounds are known to be stagnant in the inflammatory stage, causing excessive inflammatory reactions, resulting in abnormal increases in pro-inflammatory cytokine and MMPs (Eming S A, Krieg T, Davidson J M (2007) Inflammation in Wound Repair: Molecular and Cellular Mechanisms. *Journal of Investigative Dermatology.* 127:514-525.).

Also, the expression of growth factors is reduced, and the process of vasogenesis and the formation of granulation tissue are not done properly (Frank S, Hubner G, Breier G, Longaker M T. Greenhalgh D G, Werner S (1995)

Regulation of Vascular Endothelial Growth Factor Expression in Cultured Keratinocytes. *Journal of Biological Chemistry.* 270: pp. 12607-12613.; Goldman R (2004) Growth Factors and Chronic Wound Healing: Past, Present, and Future. *Advances in Skin & Wound Care.* 17: pp. 24-35.).

A chronic wound is characterized that the wound has not healed naturally within three months and occurs in patients with diabetes and vascular disease. (Nunan R, Harding K G, Martin P (2014) Clinical challenges of chronic wounds: searching for an optimal animal model to recapitulate their complexity. *Disease Models & Mechanisms.* 7:1205-1213.)

Among the chronic wounds, the largest number of patients with diabetic foot ulcers is about 400 million worldwide, 20 to 30 percent of whom are at lifetime risk of developing diabetic foot ulcers. (Armstrong D G, Boulton A J M, Bus S A (2017) Diabetic Foot Ulcers and Their Recurrence. *New England Journal of Medicine.* 376: pp. 2367-2375.).

Chronic wounds are formed by way of being not processing to the further proliferation stage, which is caused by the stagnation at the inflammatory stage, molecular biologically and for such reason, the abnormal gene expression and interaction occur thereafter (Bannon P, Wood S, Restivo T, Campbell L, Hardman M J, Mace K A (2013) Diabetes induces stable intrinsic changes to myeloid cells that contribute to chronic inflammation during wound healing in mice. *Disease Models & Mechanisms.* 6:1434-1447.).

It has been reported that the pro-inflammatory cytokines such as TNF-$\alpha$, IL-1$\beta$, IL-6 etc and MMPs (matrix metalloproteinases) are expressed as the inflammatory phase continues, whereas the expression of various growth factors such as PDGF, VEGF, and IGF etc, is decreased (Trengove N J, Bielefeldt-Ohmann H, Stacey M C (2001) Mitogenic activity and cytokine levels in non-healing and healing chronic leg ulcers. *Wound Repair and Regeneration.* 8: pp., 13-25.; Armstrong D G, Jude E B (2002) The Role of Matrix Metalloproteinases in Wound Healing. *Journal of the American Podiatric Medical Association.* 92: pp., 12-18.).

MMPs (matrix metalloproteinases) controlled by TIMPs (tissue inhibitors of metalloproteinases), decompose extracellular substrates and enables re-epithelialization. (Martins V L, Caley M. O'Toole E A (2013) Matrix metalloproteinases and epidermal wound repair. *Cell and Tissue Research.* 351:255-268)

In particular, the research on MMP-9 is the most active among MMPs, and it is known to have the most harmful effects on chronic wounds (Jones J I, Nguyen T T, Peng Z, Chang M (2019) Targeting MMP-9 in Diabetic Foot Ulcers. *Pharmaceuticals.* 12:79.; Reiss M J. Han Y P, Garcia E, Goldberg M, Yu H, Garner W L (2010) Matrix metalloproteinase-9 delays wound healing in a murine wound model. *Surgery.* 147:295-302).

Recently, a chronic wound caused by various etiology such as diabetic skin ulcers, bedsores, radiation ulcers, venous ulcers, excessive steroid use, and aging etc. give rise to experiencing problems in the normal skin injury recovery process due to the difficulty of being treated effectively. The recovering process of skin injury is suppressed due to various causes, and an abnormal inflammation in the inflammatory stage, the early stage of wound recovery, delays the progress to the proliferation stage. The loss of balance between matrix metalloproteinase (MMP) activity and TIMPs (tissue inhibitors of metalloproteinases) continues the wound injury, increases the synthesis/release of inflammatory cytokines such as TNF-alpha due to hyperactivated immune cells, and decreases in expression of growth factor such as TGF-beta, resulting in inhibiting from the progress to the proliferation stage.

In particular, delayed wound recovery of diabetic skin ulcers is attributed to blood supply disorders, neuropathy, infection, and callus production, etc and the etiology can be originated from a neovascular production, macrophage function, collagen proliferation, character of granulation tissue, a movement/activation of keratinocyte/fibroblast cell, the component of extra-cellar substrate, activity of MMP enzymes etc.

In the case of diabetic foot ulcer, about 15% of patients suffer from the damage, disability, and occlusion of peripheral blood vessels, and progress to infection, resulting in cuts in the wound area as well as the leg in the end.

As basic treatments, various treatment methods such as a blood sugar control, wound removal, dead tissue removal, and antibiotic treatment, and various forms of dressing etc, have also been developed and used in practice till now.

At present, there has been reported on some effective treatment or medicine for treating chronic wound including diabetic foot ulcer till now and various treatment methods have been developed due to a deep understanding of the physiological, biochemical and molecular biology of skin wound, for example, a high-pressure oxygen therapy for improving the ischemia occurring around wound, a skin grafting, decompression treatment, treatment of EGF, PDGF, VEGF etc, gene therapy, and stem cell therapy. (Kleopatra Alexiadou, John Doupis (2012) Management of Diabetic Foot Ulcers. Diabetes Ther. Dec; 3 (1): 4; Aurelio Perez-Favila, Margarita L Martinez-Fierro, Jessica G Rodriguez-Lazalde (2019 Current Therapeutic Strategies in Diabetic Foot ulcers. Medicina, 55 (11), 714).

In particular, a number of studies have been conducted on growth factors to recover the diabetic skin ulcers, including IGF (insulin-like growth factor), TGF-alpha, VEGF, bFGF, PDGF (platelet-derived growth factor). NGF (nerve growth factor), GM-CSF (granulocyte-macrophage colony stimulating factor), EGF (endothelial growth factor), HGF (hepatocyte growth factor) etc. ((Grazul-Bilska A T (2003) Wound healing: the role of growth factors. Drugs Today (Barc) 2003 October; 39 (10): 787-800).

A growth factor, as one of wound treating agent such as recombinant PDGF (local spreading agent, Becaplermin®, Regranex), VEGF (local spreading agent, Telbermin®, Genentech Inc.) etc has been reported to show treating effects. However, their use has some limitation to use and has been greatly reduced recently due to high cost, safety problem such as risk on the occurrence of cancer etc. (McLaughlin P J, Cain J D, Titunick M B, Sassani J W, Zagon I S. Topical Naltrexone Is a Safe and Effective Alternative to Standard Treatment of Diabetic Wounds. Adv Wound Care. 2017; 6:279-288.).

Additionally, these growth factor treatments are not effectively delivered by MMPs in wound areas, so they have to be treated frequently at high concentrations and their actual effects are not consistent. In addition, in the case of recombinant growth factors, their skin tissue permeability decreases, which requires about 50 times the amount needed for recovery in the actual tissue, resulting in a high-priced problem.

As one of wound treating agents, stem cell therapy, which has been in the spotlight recently, also requires a lot of research to apply to clinical trials. (Lara Lopes, Ocean Setia, Afsha Aurshina, Shirley Liu, Haidi Hu (2018) Stem cell therapy for diabetic foot ulcers: a review of preclinical and clinical research. Stem Cell Res Ther: 9:188)

As one of wound treating agents, cephalexin and clindamycin are commonly used as antibiotics, while ampicillin and imipenem are used for moderate or chronic infections.

Accordingly, there has been still needed to develop more effective drug and cosmetics in treating and alleviating skin wound or ulcer such as diabetic foot ulcer from natural resources with low side effects and low cost than conventionally used drugs till now.

Longanae Arillus, a seed coat of *Dimocarpus longan, Euphoria longan* or the same species belonged to Sapindaceae has been reported to contain a glucose, fructose, protein etc and to show cardio-protective effect, appetite stimulating effect etc (Chung B. S et al, Dohaehyangyakdaesajeon, youngrimsa, $2^{nd}$ Ed. p 197-198, 1998).

Ligustici Tenuissimi Rhizoma, a rhizoma or root of *Ligusticum tenuissimum Kitagawa, Ligusticum sinense Oliv, Ligusticum jeholense* Nakai et Kitagawa or the same species belonged to Umbelliferae has been reported to contain a endolide, 3-butyl phthalide etc and to show anti-bacterial effect etc (Chung B. S et al, Dohaehyangyakdaesajeon, youngrimsa, $2^{nd}$ Ed. P 428-429, 1998).

Polygalae radix, a root of Polygala *tenuifolia* Willd., or the same species belonged to Polygalaceae has been reported to contain various sanponis and to show expectorant activity, anti-bacterial effect etc (Chung B. S et al, Dohaehyangyakdaesajeon, youngrimsa, 2nd Ed. P 798-799, 1998).

However, there has been not reported or disclosed on the preventing or alleviating activity of a topically applied extract of combined herbs of Longanae Arillus Ligustici Tenuissimi Rhizoma and Polygalae radix showing potent treating effect on skin wound or ulcer such as diabetic foot ulcer in any of above cited literatures, and the disclosures of which are incorporated herein by reference.

DISCLOSURE OF INVENTION

Technical Problem

To investigate the treating or alleviating effect of a combined herb extract of Longanae Arillus, Ligustici Tenuissimi Rhizoma and Polygalae radix on skin wound or ulcer such as diabetic foot ulcer, the inventors of present invention have intensively carried out various experiments including in vitro experiments such as inhibitory effect on cytokine expression (in vitro). (Experimental Example 1); Promoting effect on cell proliferation (in vitro). (Experimental Example 2); Recovering effect on cell wound (in vitro) (Experimental Example 3); as well as in vivo experiments such as the treating effect on chronic ulcer (in vivo) (Experimental Example 4); recovering effect on skin wound (in vivo) (Experimental Example 5); inhibitory effect on the expression of pro-inflammatory cytokines involved in growth factor (in vivo) (Experimental Example 6). As a result of these investigations, the inventors finally completed the present invention by confirming that inventive combined herb extract strongly inhibited and alleviate skin ulcer.

Solution to Problem

The technical solution to solve the problem of the background art is for the development of novel herb formulation for treating and preventing a skin ulcer.

Accordingly, it is an object of the present invention to provide a topical pharmaceutical composition comprising a combined herb extract of Longanae Arillus, Ligustici Tenuissimi Rhizoma and Polygalae radix as an active ingredient to treat and alleviate skin ulcer.

The term "combined herb extract" defined herein comprises the combined herb extract, i.e., (a) combined herb extract of Longanae Arillus, Ligustici Tenuissimi Rhizoma and Polygalae radix with the mixed ratio based on the dried weight of Longanae Arillus, Ligustici Tenuissimi Rhizoma and Polygalae radix (w/w) ranging from 0.01-100:0.01-100:0.01-100 weight part (w/w), preferably. 0.1-50:0.1-50:0.1-50 weight part (w/w), more preferably, 0.1-10:0.1-10:0.1-10 weight part (w/w), more and more preferably. 1-5:1-5:1-5 weight part (w/w), most preferably. 1-3:1-3:1-3 weight part (w/w); or (b) the combination of each extract of Longanae Arillus, Ligustici Tenuissimi Rhizoma and Polygalae radix with the mixed ratio based on the dried weight of Longanae Arillus, Ligustici Tenuissimi Rhizoma and Polygalae radix (w/w) ranging from 0.01-100:0.01-100:0.01-100 weight part (w/w), preferably, 0.1-50:0.1-50:0.1-50 weight part (w/w), more preferably, 0.1-10:0.1-10:0.1-10 weight part (w/w), more and more preferably, 1-5:1-5:1-5 weight part (w/w), most preferably, 1-3:1-3:1-3 weight part (w/w) in the present invention.

it is an another object of the present invention to provide a TLSP expression inhibitor comprising a combined herb extract of Longanae Arillus. Ligustici Tenuissimi Rhizoma and Polygalae radix as an active ingredient in an amount to inhibit TLSP (thymic stromal lymphopoietin) cytokines.

The term "extract" disclosed herein, not limited thereto, comprises the extract which can be extracted with at least one solvent selected from water, $C_1$-$C_4$ lower alkyl alcohol such as methanol, ethanol, propanol, butanol, etc, acetone, ethyl acetate, chloroform, hexane, butyleneglycol, propyleneglycol or glycerin, preferably, water, methanol, ethanol, more preferably, water or 10-90% (v/v) ethanol in water, most preferably, water or 20-80% (v/v) ethanol in water.

The term "skin ulcer" disclosed herein, not limited thereto, comprises a decubitus ulcer, diabetic ulcer or and the like.

Inflammation is part of the complex biological response of body tissues to harmful stimuli, such as pathogens, damaged cells, or irritants, and the nonspecific immune response such as heat, pain, redness, swelling, etc is called as "inflammatory response" Inflammation can be classified as (a) acute inflammation, the initial response of the body to harmful stimuli, is achieved by the increased movement of plasma and leukocytes (especially granulocytes) from the blood into the injured tissues and then a series of biochemical events propagates and matures the inflammatory response, involving the local vascular system, the immune system, and various cells within the injured tissue and (b) Prolonged inflammation, known as chronic inflammation, leading to a progressive shift in the type of cells present at the site of inflammation, such as mononuclear cells, and being characterized by simultaneous destruction and healing of the tissue from the inflammatory process.

Generally, the macrophage in damaged cell excrete various cytokines, which activates T lymphocyte and mast cell, a lymphocyte, releases various histamines, which initiate internal barrier response, resulting in inducing inflammation of the inflected cells. Accordingly, the expressed level of cell cytokines may be used as an indicator of the activation of inflammatory response (the other aspects, anti-inflammatory activity). The "anti-inflammatory activity" disclosed herein denotes the inhibitory activity against various skin inflammation.

Cytokines means all the immunological substances including chemokines, interferons, interleukins, lymphokines, and tumour necrosis factors produced by a broad range of cells, including immune cells like macrophages, B lymphocytes, T lymphocytes and mast cells, as well as endothelial cells, fibroblasts, and various stromal cells, which are released through immunological progress caused by the infiltration of various pathogen such as virus etc.

Generally, cytokines are released at initial stage of infection, however, released constantly where the immune system becomes extraordinarily activated. When the high-level of cytokines are released for a long time such as more than week, we called as "a cytokine storm", which is a physiological reaction in which the innate immune system causes an uncontrolled and excessive release of pro-inflammatory signaling molecules called cytokines and it exacerbates the inflammation resulting from the extremely abundant homing of immune cells to the inflected area, causes to blood extravasation through the loosening of blood vessel and severely to death. The term "the inhibitory activity of cytokine expression" disclosed herein can be interpreted as a prevention, treatment or improvement of cytokine storm.

The term "cytokine" disclosed herein, not intended to limit thereto, comprises various cytokine involved in dermatitis, such as atopic dermatitis, specifically, the cytokine selected from group of TLSP (thymic stromal lymphopoietin), colony stimulating factor (CSF) such as GM-CSF (granulocyte-macrophage colony stimulating factor), M-CSF (macrophage colony stimulating factor), G-CSF (granulocyte colony stimulating factor) and the like, interleukins such as interleukin-1 (IL-1). IL-4, IL-10, IL-12, IL-13, IL-31, IL-33 and the like, tumor necrosis factor alpha (TNF-$\alpha$), interferon gamma (IFN$\gamma$) etc, An inventive extract may be prepared in accordance with the following preferred embodiment.

For the present invention, above described extract can be prepared by follows;

The term "combined herb extract of Longanae Arillus, Ligustici Tenuissimi Rhizoma and Polygalae radix" defined herein can be prepared by the procedure comprising the steps; of slicing and washing Longanae Arillus, Ligustici Tenuissimi Rhizoma and Polygalae radix" to use as a basic extraction material at $1^{st}$ step; mixing together thoroughly with the mixed ratio based on the dried weight of Longanae Arillus, Ligustici Tenuissimi Rhizoma and Polygalae radix (w/w) ranging from 0.01-100:0.01-100:0.01-100 weight part (w/w), preferably, 0.1-50:0.1-50:0.1-50 weight part (w/w), more preferably, 0.1-10:0.1-10:0.1-10 weight part (w/w), more and more preferably, 1-5:1-5:1-5 weight part (w/w), most preferably, 1-3:1-3:1-3 weight part (w/w) to afford the mixed material at 2nd step; adding 1-20 fold volume (v/w), preferably, 4-8 fold volume (v/w) of extracting solvent selected from the group consisting of water, $C_1$-$C_4$ lower alkyl alcohol such as methanol, ethanol, propanol, butanol, etc, acetone, ethyl acetate, chloroform, hexane, butyleneglycol, propyleneglycol or glycerin, preferably, water, methanol, ethanol, more preferably, water or 10-90% (v/v) ethanol in water, most preferably, water or 20-80% (v/v) ethanol in water to the mixed material at 3rd step; extracting each solution with the extraction method by the extraction with hot water extraction, cold water extraction, reflux extraction or ultra-sonication extraction, preferably, hot water extraction at the temperature ranging from 50° C. to 120° C., preferably, about 80° C. to 100° C., for the period ranging from 1 to 24 hours, preferably, 2 to 12 hours at 4th step; repeating the above-described extraction process to collect each filtrate with filtration, drying through freeze drying, natural air drying or hot air drying process, preferably freeze drying process to obtain the combined herb extract of Longanae Arillus, Ligustici Tenuissimi Rhizoma and Polygalae radix of the present invention.

It is another object of the present invention to provide a process for preparing the combined herb extract of Longanae Arillus, Ligustici Tenuissimi Rhizoma and Polygalae radix of the present invention, as described above.

It is another object of the present invention to provide a topical pharmaceutical composition comprising a combined herb extract of Longanae Arillus, Ligustici Tenuissimi Rhizoma and Polygalae radix prepared by the above-described process, as an active ingredient to treat and alleviate skin ulcer.

In accordance with another aspect of the present invention, there is also provided a method of treating or alleviating skin ulcer in a mammal comprising topically administering to said mammal an effective amount of the combined herb extract of Longanae Arillus, Ligustici Tenuissimi Rhizoma and Polygalae radix and pharmaceutically acceptable carrier thereof.

In accordance with the other aspect of the present invention, there is also provided a use of the combined herb extract of Longanae Arillus, Ligustici Tenuissimi Rhizoma and Polygalae radix for manufacture of topical preparation employed for treating or alleviating skin ulcer in mammals including human as an active ingredient.

The inventive composition may additionally comprise conventional carrier, adjuvants or diluents in accordance with a using method. It is preferable that said carrier is used as appropriate substance according to the usage and application method, but it is not limited. Appropriate diluents are listed in the written text of Remington's Pharmaceutical Science (Mack Publishing co, Easton PA).

Hereinafter, the following formulation methods and excipients are merely exemplary and in no way limit the invention.

The inventive composition according to the present invention can be provided as a topical pharmaceutical composition containing pharmaceutically acceptable carriers, adjuvants or diluents. e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

For topical administration, the inventive extract of the present invention can be formulated in the form of ointments and creams including topical preparation such as cream, gel, patch, spray solution, emulsion, ointment, lotion, liniment, balm, solution, suspension, pack, paste, aerosol, cataplasma and the like.

The inventive composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or composition varies depending on the condition and the weight of the subject, severity, drug form, route and period of administration, and may be chosen by those skilled in the art. However, in order to obtain desirable effects, it is generally recommended to topically administer at the amount ranging 0.01-10 g/kg, preferably. 1 to 5 g/kg by weight/day of the inventive extract of the present invention. The dose may be administered in a single or multiple doses per day. In terms of composition, the inventive extract should be present between 0.01 to 80% by weight, preferably 0.5 to 50% by weight based on the total weight of the composition.

The present inventors demonstrated that the anti-inflammatory effects of inventive composition are potent by accomplishing in vitro experiments such as inhibitory effect on cytokine expression (in vitro). (Experimental Example 1); Promoting effect on cell proliferation (in vitro). (Experimental Example 2); Recovering effect on cell wound (in vitro) (Experimental Example 3); as well as in vivo experiments such as the treating effect on chronic ulcer (in vivo) (Experimental Example 4); recovering effect on skin wound (in vivo) (Experimental Example 5); inhibitory effect on the expression of pro-inflammatory cytokines involved in growth factor (in vivo) (Experimental Example 6), therefore, it is confirmed that inventive combined extract is very useful in the alleviation or treatment of skin ulcer as a form of topical medicament or cosmetic composition.

It is the other object of the present invention to provide a cosmetic composition comprising the combined herb extract of Longanae Arillus, Ligustici Tenuissimi Rhizoma and Polygalae radix as an active ingredient in an amount effective to treat and alleviate skin ulcer.

It is preferable that the present cosmetic composition contains 0.001-40%, more preferably, 0.01-10% by the weight of the inventive composition based on the total weight of the composition. The other components may be a mixture of the ingredients of a conventional cosmetic composition well known in the art.

Cosmetic formulations containing above composition may be prepared in any form such as skin lotion, skin softener, skin toner, astringent, lotion, milk lotion, moisture lotion, nutrient lotion, massage cream, nutrient cream, moisture cream, hand cream, foundation, essence, nutrient essence, pack, cleansing foam, cleansing lotion, cleansing cream, body lotion, body cleanser, treatment, beauty solution and the like.

Hereinafter, the following formulation methods and excipients are merely exemplary and in no way limit the invention.

The cosmetic composition of the present invention can comprises additional additives selected from the group consisting of water soluble vitamin, lipid soluble vitamin, peptide polymer, polysaccharide polymer, sphingolipid and sea-weed extract.

Preferable water soluble vitamins are any one which can be mixed with cosmetic, however, various vitamin such as vitamin $B_1$, $B_2$, $B_6$, pyridoxine, pyridoxine HCl, vitamin $B_{12}$, pantothenic acid, nicotinic acid, nicotinamide, folic acid, vitamin C, vitamin H etc, the salt thereof such as thiamin HCl salt, ascorbic acid Na salt etc or their derivatives such as ascorbic acid-2-phosphonic acid Na salt, ascorbic acid-2-phosphonic acid Mg salt are preferable and those can be obtained by conventional method such as microbial conversion method, purification method from the microbial cultivates, enzymatic method or chemical synthetic method.

Preferable lipid soluble vitamins are any one which can be mixed with cosmetic, however, various vitamin such as vitamin A, $D_2$, $D_3$, E (dl-a-tocopherol, da-tocopherol, d-d-tocopherol) and their derivatives such as palmitic acid ascorbate, stearic acid ascorbate, dipalmitic acid ascorbate, acetic acid-dl-a-tocopherol, nicotinic acid dl-a-tocopherol vitamin E, dl-pantothenyl alcohol, D-pantothenyl alcohol, pantothenyl ethylether etc. including the lipid soluble vitamin used in examples of present invention are preferable and those can be obtained by conventional method such as microbial conversion method, purification method from the microbial cultivates, enzymatic method or chemical synthetic method.

Preferable peptide polymers are any one which can be mixed with cosmetic, however, collagen, hydrolysable collagen, gelatin, elastin, hydrolysable gelatin, keratin etc. including the peptide polymer used in examples of present invention are preferable.

Preferable polysaccharide polymers are any one which can be mixed with cosmetic, however, hydroxy ethyl cellulose, xanthin gum, hyaluronic acid Na, chondroitin sulfate or their salt (Na salt etc) and the like are preferable. For example, chondroitin sulfate or the salt thereof etc can be used by being purified from mammal or fishes ordinarily.

Preferable sphingolipid are any one which can be mixed with cosmetic, however, ceramide, pit-sphingosin, sphingo-lipopolysaccharide and the like are preferable. Sphingo-lipid can be obtained by being purified from mammal, fish, shellfish, yeast or plant etc in conventional method.

Preferable seaweed extract is any one which can be mixed with cosmetic, however, the extract of brown algae, red algae, green algae and the like or the purified carrageenan, alginic acid, arginic acid Na, K isolated therefrom are preferable. Algae extract can be obtained by being purified from seaweed in conventional method.

The cosmetic composition of the present invention may combine with other ingredients used in conventional cosmetic composition, if necessary, together with above described essential ingredient.

Preferable above described other ingredients may comprise oil ingredient, humectants, emollients, surfactants, organic or inorganic dye, organic powder, ultraviolet ray absorbing agent, preservatives, antiseptics, antioxidants, plant extract, pH controller, alcohol, pigments, perfumes, refrigerants, blood circulator, antihidrotic, distilled water etc.

Preferable oil ingredients may comprise ester oil, hydrocarbon oil, silicone oil, fluoride oil, animal oil, plant oil and so on.

Preferable ester oil described above may comprise glyceryl tri-2-ethyl hexanoic acid, cetyl 2-ethyl hexanoic acid, isopropyl myristic acid, butyl myristic acid, isopropyl palmitic acid, ethyl stearic acid, octyl palmitic acid, isocetyl isostearic acid, butyl stearic acid, ethyl linoleic acid, isopropyl linoleic acid, ethyl oleic acid, isocetyl myristic acid, isostearyl myristic acid, isostearyl palmitic acid, octyldodecyl myristic acid, isocctyl isostearic acid, diethyl sebasic acid, isopropyl adipic acid, isoalkyl neopentanoic acid, glyceryl tri (capryl, capric acid), trimethylolpropane tri-2-ethyl hexanoic acid, trimethylolpropane triisostearic acid, pentaerythritol tetra-2 ethyl hexanoic acid, cetyl caprylic acid, decyl lauric acid, hexyl lauric acid, decyl myristic acid, myristyl myristic acid, cetyl myristic acid, stearyl stearic acid, decyl oleic acid, cetyl licinoleic acid, isostearyl lauric acid, isotridecyl myristic acid, isocetyl palmitic acid, octyl stearic acid, isocetyl stearic acid, isodecyl oleic acid, octyldodecyl oleic acid, octyldodecyl linoleic acid, isopropyl isostearic acid, cetostearyl 2-ethyl hexanoic acid, stearyl 2-ethyl hexanoic acid, hexyl isostearic acid, ethylene glycol dioctanoic acid, ethylene glycol dioleic acid, propylene glycol dicapric acid, propylene glycol di(capryl, capric acid), propylene glycol dicaprylic acid, neopentylglycol dicapric acid, neopentylglycol dioctanoic acid, glyceryl tricaprylic acid, glyceryl triundecylic acid, glyceryl triisopalmitic acid, glyceryl triisostearic acid, octyldodecyl neopentanoic acid, isostearyl octanoic acid, octyl isononanoic acid, hexyldecyl neodecanoic acid, octyldodecyl neodecanoic acid, isocetyl isostearic acid, isostearyl isostearic acid, octyldecyl isostearic acid, polyglycerin oleanoic acid ester, polyglycerin isostearic acid ester, triisocetyl citric acid, triisoalkyl citric acid, triisooctyl citric acid, lauryl lactic acid, myristyl lactic acid, cetyl lactic acid, octyldecyl lactic acid, triethyl citric acid, acetyltriethyl citric acid, acetyl tributyl citric acid, trioctyl citric acid, diisostearyl maleic acid, di 2-ethylhexyl hydroxy stearic acid, 2-ethyl hexyl succinic acid, diisobutyl adipic acid, diisopropyl sebasinic acid, dioctyl sebacinic acid, cholesteryl stearic acid, cholesteryl isostearic acid, cholesteryl hydroxy stearic acid, cholesteryl hydroxy stearic acid, cholesteryl oleic acid, dihydrocholesteryl oleic acid, pitsteryl isostearic acid, pitsteryl olcic acid, isocctyl 12-stealoyl hydroxy stearic acid, stearyl 12-stealoyl hydroxy stearic acid, isostearyl 12-stealoyl hydroxy stearic acid.

Preferable hydrocarbon oil described above may comprise squalene, liquid paraffin, α-olefin oligomer, isoparaffin, ceresin, paraffin, liquid isoparaffin, polybuden, microcrystalline wax, vaselin and the like.

Preferable silicone oil may comprise polymethylsilicone, methylphenylsilicone, methylcyclopolysiloxane, octamethylpolysiloxane, decamethylpolysiloxane, dodecamethylcyclosiloxane, dimethyl siloxane-methyl cetyloxysiloxan copolymer, dimethyl siloxane-methyl stealoxysiloxane copolymer, alkyl modified silicone oil, amino modified silicone oil and the like.

Preferable fluoride oil can comprise perfluoropolyether and the like.

Preferable animal or plant oil can comprise avocado oil, almond oil, olive oil, sesame oil, rice husk oil, safflower oil, soy-bean oil, corn oil, rape oil, amygdalin oil, palm kernel oil, palm oil, pimaja oil, sunflower oil, fruite seed oil, cotton seed oil, coconut palm oil cucui nut oil, wheat embryo bud oil, rice embryo bud oil, sia butter, evening-primrose oil, marker daymia nut oil, mcdo home oil, egg yolk oil, lanolin, hempseed oil, mink oil, orange ruppy oil, hohoba oil, carnawa wax, liquid lanolin, solid pimaja wax and the like.

Preferable humectants can comprise water-soluble low molecular humectants, lipophilic low molecular humectants, water-soluble polymer and lipid soluble polymer.

Specifically, preferable water soluble low molecular humectants can comprise cerin, glutamine, sorbitol, mannitol, pyrrolidone-carboxylic acid Na, glycerin, propylene glycol, 1,3-butylene glycol, ethylene glycol, polyethylene glycol (polymerization index. >2), polypropylene glycol (polymerization index>2), lactic acid, lactate salt and the like.

Preferable lipid soluble low molecular humectants can comprise cholesterol, cholesteryl ester and the like.

Preferable water soluble polymer can comprise carboxy vinyl polymer, poly asparaginic acid salt, tragacanth, xanthin gum, HMC (hydroxy methyl celluose), HEC (hydroxy ethyl celluose), HPC (hydroxy propyl celluose), carboxymethylcellulose, water soluble chitin, chitosan, dextrin and the like.

Preferable lipid soluble polymer can comprise polyvinylpyrrolidone-eicocene copolymer, polyvinylpyrrolidone-hexadecene copolymer, nitrocellulose, dextrin fatty acid ester, silicone polymer and the like.

Preferable emollients can comprise long chain acyl glutamic acid cholesteryl ester, cholesteryl hydroxy stearic acid, 12-hydroxy stearic acid, rogic acid, lanolin fatty acid cholesteryl ester and the like.

Preferable surfactant can comprise nonionic surfactants, anionic surfactants, cationic surfactants, ambivalent surfactants and the like.

Specifically, preferable non-ionic surfactants can comprise self-emulsified monostearic acid glycerin, propylene glycol fatty acid ester, glycerin fatty acid ester, polyglycerin fatty acid ester, sorbitan fatty acid ester, polyoxyethylene (POE) sorbitan fatty acid ester, POE sorbitan fatty acid ester, POE glycerin fatty acid ester, POE alkyl ether, POE fatty acid ester, POE solid pimaja oil, POE pimaja oil, POE-POP copolymer. POE-POP alkyl ether, polyether modified silicone, lauric acid alkanol amide, alkyl amine oxide, hydrogen addition soybean phospholipid and the like.

Preferable anionic surfactants can comprise fatty acid soap, a-acyl sulfonic acid salt, alkyl sulfonic acid salt, alkyl ally sulfonic acid, alkyl naphthalene sulfonic acid salt, alkyl sulfonic acid salt, POE alkylether sulfate salt, alkyl amide sulfate salt, alkyl phosphate salt, POE alkyl phosphate salt, alkylamide phosphate salt, alkyloylalkyl taurine salt, N-acyl-amino acid salt, POE alkyl ether carboxylic acid salt, alkyl sulfo succinic aid salt, alkyl sulfo-acetic acid salt, acylated hydrolysable collagen peptide salt, perfluoro alkyl phosphate ester and the like.

Preferable cationic surfactant can comprise alkyl trimethyl ammonium chloride, stearyl trimethyl ammonium chloride, stearyl trimethyl ammonium bromide, setostearyltrimethyl ammonium chloride, distearyl dimethyl ammonium chloride, stearyl dimethyl benzyl ammonium chloride, vehenyltrimethyl ammonium bromide, benzalkonium chloride, diethylamino ethyl amide stearic acid, dimethylaminopropyl amide stearic acid, lanolin derivatives quaternary ammonium and the like.

Preferable ambivalent surfactants can comprise carboxy betaine type, amide betaine type, hydroxy sulfo betaine type, phosphobetaine type, aminocarboxylic acid, imidazoline derivatives type, amide amine type and the like.

Preferable organic and inorganic dyes can comprise silicic acid, anhydrous silicic acid, magnesium silicic acid, tale, ceracyte, mica, caolin, bengala, clay, bentonite, titan film mica, oxy chlorine bismuth, zirconium oxide, magnesium oxide, zinc oxide, titan oxide, aluminium oxide, calcium sulfate, barium sulfate, magnesium sulfate, calcium carbonate, magnesium carbonate, ferrous oxide, chromium oxide, chromium hydroxide, calamine, carbon black and the complex thereof as an inorganic dyes; polyamide, polyester, polypropylene, polystyrene, polyurethane, vinyl resin, urea resin, phenol resin, fluoride resin, silicone resin, acryl resin, melamine resin, epoxy resin, polycarbonated resin, divinyl benzene-styrene copolymer, silk powder, cellulose, CI pigment yellow, CI pigment orange as an organic dyes; and their complex etc.

Preferable organic powder can comprise metal soap such as calcium stearate; alkyl phosphonate metal salt such as sodium zinc cetylic acid, zinc laurylic acid, calcium laurylic acid; acylamino acid polyvalent metal salt such as calcium N-lauroyl-b-alanine, zinc N-lauroyl-b-alanine, calcium N-lauroyl-glycine etc.; amide sulfonic acid polyvalent metal salt such as calcium N-lauroyl-taurine, calcium N-palmitoyl-taurine; N-acyl basic amino acid such as Ne-lauroyl-L-lysine, Nε-palmitoyl-lysine, Na-palmitoyl ornitine, Na-lauroly arginine, hardened lanolin fatty acid acyl arginine and the like; N-acylpolypeptide such as N-lauroylglycyl glycine; a-amino fatty acid such as a-amino caprylic acid, α-amino lauric acid and the like; polyethylene, polypropylene, nylon, polymethylmetacrylate, polystyrene, divinylbenzene-styrene copolymer, ethylene tetrafluoride and so on.

Preferable ultraviolet absorbing agents can comprise paraaminobenzoic acid, para-monoethyl benzoate, paraamino amyl benzoate, paraamino octyl benzoate, ethyleneglycol salicylate, phenyl salicylate, octyl salicylate, benzyl salicylate, butylphenyl salicylate, homomentyl salicylate, benzyl cinnamic acid, paramethoxy 2-ethoxy ethyl cinnamic acid, paramethoxy octyl cinnamic acid, diparamethoxy mono-2-ethylhexane glyceryl cinnamic acid, paramethoxy isopropyl cinnamic acid, diisopropyl-diisopropyl cinnamate ester mixture, urokanic acid, ethyl urokanic acid, hydroxy methoxy benzophenone, hydroxymethoxy benzophenone sulfonic acid and their salt, dihydroxy methoxy benzophenone, dihydroxy methoxy benzophenone disulfonate Na, dihydroxy benzophenone, tetrahydroxybenzophenone, 4-tertbutyl-4'-methoxydibenzoylmethane, 2,4,6- trianilino-p(carbo-2'-ethylhexyl-1'-oxy)-1,3,5-triazine, 2-(2-hydroxy-5-methylphenyl)benzotriazole and the like.

Preferable preservatives can comprise hinokitiol, trichloric acid, trichlorohydroxy-diphenylether, chlorohexidine glucuronate, phenoxyethanol, resorcine, isopropyl-methylphenol, azulene, salicylic acid, zinc pilithione, bezalconium HCl, photosensitizer 301, mononitroguaiacol Na, undecylenic acid etc.

Preferable antioxidants can comprise butylhydroxyanisole, propyl gallate, ellisorbate and the like.

Preferable pH controller can comprise citric acid, sodium citrate, malic acid, sodium malate, fumaric acid, sodium fumaric acid, succinic acid, sodium succinic acid, sodium hydroxide, sodium hydrogen phosphate and the like.

Preferable alcohol can comprise cetyl alcohol etc.

Furthermore, other ingredient addable to above described component and the amount thereof is not limited within the scope of the purpose and effect of the present invention, however, it is preferable that the amount of the other ingredients ranges from 0.01 to 5%, more preferably. 0.01 to 3% in that of total composition.

The cosmetic composition of the present invention can be modified as a solution, emulsion, cohesive mixture etc.

Above described ingredients such as water-soluble vitamin, lipid soluble vitamin, peptide polymer, polysaccharide polymer, sphingolipid, sea weed extract and addable ingredients which can be added other than above described ingredients if necessary, can be obtained by conventional methods disclosed in the literature (Matsumoto Mithio; Manual for the development of transdermal applied preparation. Seisi Press, 1$^{st}$ Ed., 1985).

Inventive compounds of the present invention have no toxicity and adverse effect therefore, they can be used with safe.

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

Advantageous Effects of Invention

As described above, the present inventors demonstrated that the anti-ulcer effects of inventive combined composition are potent by accomplishing in vitro experiments such as inhibitory effect on cytokine expression (in vitro). (Experimental Example 1); Promoting effect on cell proliferation (in vitro). (Experimental Example 2); Recovering effect on cell wound (in vitro) (Experimental Example 3); as well as in vivo experiments such as the treating effect on chronic ulcer (in vivo) (Experimental Example 4); recovering effect on skin wound (in vivo) (Experimental Example 5); inhibitory effect on the expression of pro-inflammatory cytokines involved in growth factor (in vivo) (Experimental Example 6), therefore, it is confirmed that inventive combined extract is very useful in the alleviation or treatment of skin ulcer as a form of topical medicament or cosmetic composition.

BRIEF DESCRIPTION OF DRAWINGS

FIG. 1 shows the cell photography in the test group treated with inventive combined extract after scratching skin epithelial cells (HaCaT)(DIW: distilled water; NP: inventive combined extract);

FIG. 2 shows the establishment of streptozotocin (STZ)-induced diabetic mouse model (STZ: streptozotocin, DIW: distilled water; NP: inventive combined extract);

FIG. 3 represents the healing effect of inventive combined extract (NP) on diabetic skin wound healing according to post-injury day (Con: Control group; STZ: streptozotocin, DIW: distilled water; NP: inventive combined extract);

FIG. 4 depicts the histological analysis of diabetic skin wound and promoting effect of inventive combined extract (NP) on the proliferation of granulation tissue (Scale bars=200 μm, STZ: streptozotocin, DIW: distilled water; NP: inventive combined extract)).

BEST MODE FOR CARRYING OUT THE INVENTION

It will be apparent to those skilled in the art that various modifications and variations can be made in the compositions, use and preparations of the present invention without departing from the spirit or scope of the invention.

The present invention is more specifically explained by the following examples. However, it should be understood that the present invention is not limited to these examples in any manner.

EXAMPLES

The following Examples and Experimental Examples are intended to further illustrate the present invention without limiting its scope.

Example 1. The Preparation of Inventive Combined Extract (1)

20 g of dried Longanae Arillus (Buyoung Yakup Co. Ltd.), 20 g of dried Ligustici Tenuissimi Rhizoma (Buyoung Yakup Co. Ltd.) and 20 g of dried Polygalae radix (Buyoung Yakup Co. Ltd.) were cut into small pieces, mixed with 6 fold volume (v/w) of 20% ethanol in water and the mixture was subjected to reflux extraction at 90±5° C. for 3 days. After filtration of the extract through filter paper (pore size, less than 10 μm) to remove the debris, the remaining debris was further extracted two times with 4 fold volume (v/w) of 20% ethanol in water and the extract was filtered with filter paper (pore size, less than 10 μm).

The collected extract was mixed with together and concentrated under vacuo (16-21 brix) to afford concentrated extract. The concentrated extract was dried with freeze drying process and pulverized (less than 50 mesh) to obtain 20.5 g (powder as dried basis, yield 33.4%) of inventive combined extract (1) (designated as "WIN-1001X" hereinafter)

Example 2-6. The Preparation of Inventive Combined Extract (2)-(6)

Excepting adopting different combined ratio as well as different solvents disclosed in Example 1, all the procedure was identical with those in Example 1 to obtain various inventive combined extract of Longanae Arillus (LA), Ligustici Tenuissimi Rhizoma (LT) and Polygalae radix (PR) i.e., inventive combined extract (2) to inventive combined extract (6) of the present invention, which are used as a test samples in following experiment.

TABLE 1

| | various kinds of combined extract | | | | | | |
|---|---|---|---|---|---|---|---|
| | Sample weight (g) | | | | | Extract | Final |
| Example | LA* | PR* | LT* | solvent* | name | weight | yield |
| Example 2 | 10 | 5 | 50 | 10% EtOH | WIN-1002X | 16.6 g | 25.6% |
| Example 3 | 20 | 50 | 5 | Water | WIN-1003X | 24.7 g | 32.9% |
| Example 4 | 10 | 80 | 20 | 70% BuOH | WIN-1004X | 32.3 g | 29.4% |
| Example 5 | 5 | 50 | 20 | 50% EtOH | WIN-1005X | 21.5 g | 28.7% |
| Example 6 | 30 | 10 | 2 | hexane | WIN-1006X | 12.6 g | 30.1% |

*Longanae Arillus (LA), Ligustici Tenuissimi Rhizoma (LT), Polygalae radix (PR)

Experimental Example 1. Inhibitory Effect on Cytokine Expression (In Vitro)

In order to determine the anti-inflammatory activity of inventive extract, following inhibition test of cytokine expression using HaCaT cell was performed according to the procedure disclosed in the literature (Jeong et al., 2019, J. Invest. Dermatol., May; 139 (5): pp 1098-1109).

HaCaT cell (human epithelial keratinocyte cell, 300493, CLS) was inoculated into DMEM medium containing 10% Fetal bovine serum, 100 units/ml of penicillin, 100 μg/ml of streptomycin (D6429, Sigma-Aldrich Co. Ltd) and was incubated in the incubator (HERA cell 150i, Thermo Fisher Scientific Co. Ltd.) maintaining optimum humidity (85-95%) and 5% $CO_2$ atmosphere.

For performing gene expression test, the incubated cells were transferred to 12 wells and 50 ng/ml of TNF alpha (RC214-12, Biobasic Co. Ltd) was treated therewith for 1 hour to induce inflammatory response. Dexamethasone (200 nM, positive control, "DEX", D4902, Sigma-Aldrich Co. Ltd.) and distilled water (negative control, "DIW") were used as comparative controls.

1 hour after inducing the inflammation, 1 μg/ml of inventive extract prepared in Examples was treated with identical medium and subjected to incubation for 1 hour. After the incubation, RNA (FATRR-001, Favorgen) was extracted from the cell and cDNA was synthesized from the RNA using by cDNA synthesis kit (RRO36A, TAKARA). The polymerization reaction was performed using by the synthesized cDNA and Sybrgreen kit (RT500M, Enzynomics) and then Real-time-PCR was performed using by primers for various cytokines involved in skin inflammation (RPLPO, TSLP, GM-CSF and IL-1beta) as disclosed in Table 2.

TABLE 2

| The used primers in RT-PCR method | | | |
|---|---|---|---|
| human* | direction | sequence | Sequence I.D |
| RPLP0 | forward | 5'-AGC CCA GAA CAC TGG TCT C-3' | 1 |
| | reverse | 5'-ACT CAG GAT TTC AAT GGT GCC-3' | 2 |
| TSLP | forward | 5'-TAT GAG TGG GAC CAA AAG TAC CG-3' | 3 |
| | reverse | 5'-GGG ATT GAA GGT TAG GCT CTG G-3' | 4 |
| GM-CSF | forward | 5'-TCC TGA ACC TGA GTA GAG ACA C-3' | 5 |
| | reverse | 5'-TGC TGC TTG TAG TGG CTG G-3' | 6 |
| IL-1β | forward | 5'-CTC CAG GGA CAG GAT ATG GA-3' | 7 |
| | reverse | 5'-TCT TTC AAC ACG CAG GAC AG-3' | 8 |

*abbreviation- RPLP0 (Ribosomal Protein Lateral Stalk Subunit P0); TSLP (thymic stromal lymphopoietin); GM (Granulocyte-macrophage)-CSF (colony stimulating factor); IL (interleukin)

As can be seen in Table 3 showing quantitative result of the RT-PCR, the test sample group treated with the inventive extract, sharply inhibited the expressed level of various cytokine involved in skin inflammation comparing with negative control group treated with distilled water (DIW) and it has been confirmed that the inhibitory activity of the test sample on the expression of various cytokine involved in skin inflammation is equivalent to that of positive control group treated with dexamethasone (DEX).

Accordingly, it has been confirmed that the various kind of inventive combined extract prepared in Examples 1-6 have potent inhibitory effect on skin inflammation.

were inoculated into DMEM medium containing 10% Fetal bovine serum, 100 units/ml of penicillin, 100 µg/ml of streptomycin (D6429, Sigma-Aldrich Co. Ltd) and was incubated in the incubator (HERA cell 150i, Thermo Fisher Scientific Co. Ltd.) maintaining optimum humidity (85-95%) and 5% $CO_2$ atmosphere.

For determining the promoting effect of inventive extract on cell proliferation, the incubated cells were transferred to 48 wells and 1 µg/ml of inventive extract prepared in Examples as well distilled water (negative control, "DIW") were treated therewith.

TABLE 3

| | Inhibition effect on cytokine expression | | | | | |
|---|---|---|---|---|---|---|
| — | TNFα DIW | TNFα WIN-1001X | TNFα WIN-1002X | TNFα WIN-1003X | TNFα WIN-1005X | TNFα Dex |
| | | | TSLP | | | |
| 1 | 132.4692 | 47.43735 | 60.85783 | 48.9323 | 55.34286 | 52.49334 |
| 0.462769 | 26.91228 | 9.645089 | 24.95619 | 19.85678 | 26.59252 | 11.2336 |
| | | | GM-CSF | | | |
| 1 | 4.473627 | 1.982161 | 2.069408 | 2.384771 | 1.917569 | 1.935997 |
| 0.111 | 0.817826 | 0.889233 | 0.326074 | 0.871501 | 0.599711 | 0.581338 |
| | | | IL-1β | | | |
| 1 | 4.152715 | 1.407169 | 1.437399 | 2.064964 | 1.662578 | 1.080503 |
| 0.483565 | 1.087056 | 0.394622 | 0.1926 | 0.620225 | 0.193175 | 0.413136 |

Experimental Example 2. Promoting Effect on Cell Proliferation (In Vitro)

In order to determine the promoting activity of inventive extract, following test of cell proliferation using HaCaT cell was performed according to the procedure disclosed in the literature (Lee et al., 2020, Int J Mol Sci. 2020 Jan. 5; 21 (1): 343).

HaCaT cell (human epithelial keratinocyte cell, 300493, CLS), Brain microvascular endothelial cells (bEND.3, CRL-2299 ATCC) and fibroblasts (NIH 3T3, CRL-1658, ATCC)

10 µL/ml of Quanti-Max™ (QM1000, BIOMAX) was repeatedly treated to the cell at the interval of 0 hr, 24 hr, 48 hr and 72 hr, respectively and subjected to incubation for 30 mins. After the incubation, the absorbance at 450 nm in each group was determined by using microplate reader (SPEC-TRA MAX 250, Molecular Devices) and the test result was shown in following Table 4.

As can be seen in Table 4, it has been confirmed that the various kind of inventive combined extract prepared in Examples 1-6 have potent promoting effect on cell proliferation.

TABLE 4

| | promoting effect on cell proliferation | | | | | | | | |
|---|---|---|---|---|---|---|---|---|---|
| | Absorbance (450 nm) | | | | SD | | | | |
| | DIW | WIN-1001X | WIN-1002X | WIN-1003X | WIN-1005X | DIW | WIN-1001X | WIN-1002X | WIN-1003X | WIN-1005X |
| | HaCaT | | | | | | | | | |
| 0 hr | | | 0.045 | | | | | 0 | | |
| 24 hr | 0.0630 | 0.0880 | 0.0793 | 0.0797 | 0.0867 | 0.0010 | 0.0069 | 0.0015 | 0.0012 | 0.0035 |
| 48 hr | 0.1987 | 0.2120 | 0.2067 | 0.2073 | 0.2073 | 0.0031 | 0.0062 | 0.0006 | 0.0025 | 0.0025 |
| 72 hr | 0.3233 | 0.3560 | 0.3513 | 0.3577 | 0.3843 | 0.0101 | 0.0082 | 0.0059 | 0.0064 | 0.0090 |
| | NIH 3T3 | | | | | | | | | |
| 0 hr | | | 0.043 | | | | | 0 | | |
| 24 hr | 0.0670 | 0.0823 | 0.0723 | 0.0720 | 0.0738 | 0.0109 | 0.0046 | 0.0057 | 0.0096 | 0.0049 |
| 48 hr | 0.1948 | 0.2170 | 0.2033 | 0.2043 | 0.2043 | 0.0186 | 0.0189 | 0.0085 | 0.0153 | 0.0153 |
| 72 hr | 0.2235 | 0.2405 | 0.2375 | 0.2308 | 0.2378 | 0.0065 | 0.0123 | 0.0114 | 0.0215 | 0.0101 |
| | bEND.3 | | | | | | | | | |
| 0 hr | | | 0.143 | | | | | 0 | | |
| 24 hr | 0.2270 | 0.2383 | 0.2187 | 0.2197 | 0.2277 | 0.0123 | 0.0067 | 0.0174 | 0.0147 | 0.0093 |
| 48 hr | 0.4100 | 0.4523 | 0.4270 | 0.4313 | 0.4313 | 0.0085 | 0.0058 | 0.0046 | 0.0081 | 0.0081 |
| 72 hr | 0.5113 | 0.5457 | 0.5440 | 0.5443 | 0.5367 | 0.0021 | 0.0040 | 0.0046 | 0.0068 | 0.0032 |

Experimental Example 3. Recovering Effect on Cell Wound (In Vitro)

In order to determine the recovering activity of inventive extract, following test of cell wound using HaCaT cell was performed according to the procedure disclosed in the literature (Na et al., 2016, J Invest Dermatol. 2016 April; 136 (4): 847-858).

HaCaT cell (human epithelial keratinocyte cell, 300493, CLS) was inoculated into DMEM medium containing 10% Fetal bovine serum, 100 units/ml of penicillin, 100 µg/ml of streptomycin (D6429, Sigma-Aldrich Co. Ltd) and was incubated in the incubator (HERA cell 150i, Thermo Fisher Scientific Co. Ltd.) maintaining optimum humidity (85-95%) and 5% $CO_2$ atmosphere.

For determining the recovering effect of inventive extract on cell wound, the incubated cells were transferred to 6 wells and incubated to the extent that the cell confluency of medium has reached to about 90%. The incubated medium was further incubated for 24 hours in serum-free medium (D6429, Sigma-Aldrich). After scratching the cultured cell with 200 µl tip (KG1212-L, Kirgen), the medium was transferred to new 2% FBS medium containing 1 µg/ml of inventive extract prepared in Examples (D6429, Sigma-Aldrich). The recovering progress was photographed and compared by hour using by microscopy (AMEX 1000, EVOS XL Core) and distilled water (negative control, "DIW") were used as a negative control group.

As can be seen in Table 5, it has been confirmed that the various kind of inventive combined extract prepared in Examples 1-6 have potent recovering effect on cell wound.

TABLE 5

| | recovering effect on cell wound | | | | |
|---|---|---|---|---|---|
| | DIW | WIN-1001X | WIN-1002X | WIN-1003X | WIN-1005X |
| 0 hr | 100.00 | 100.00 | 100.00 | 100.00 | 100.00 |
| 12 hr | 72.00 | 75.47 | 66.52 | 76.36 | 77.33 |
| 24 hr | 50.73 | 52.38 | 46.86 | 60.57 | 54.83 |
| 48 hr | 32.34 | 28.56 | 20.68 | 33.43 | 21.40 |
| 72 hr | 25.03 | 3.05 | 5.23 | 20.51 | 11.10 |

Experimental Example 4. Treating Effect on Chronic Ulcer (In Vivo)

To confirm the treating effect of inventive extract on chronic ulcer, the animal model test using by mice, was performed according to the method disclosed in the reference (Long M. Rojo de la Vega M, Wen Q, Bharara M, Jiang T. Zhang R, Zhou S, Wong P K, Wondrak G T, Zheng H, Zhang D D (2016) An Essential Role of NRF2 in Diabetic Wound Healing. *Diabetes*. 65:780-793)

4-1. Preparation of Diabetic Mouse Model 8 weeks old C57BL male mice (230 g, Daehanbiolink Co. Ltd) were raised in a breeding cage of which temperature and humidity are maintained to 22±1° C. and 50±5% and light was controlled every 12 hours and nights After acclimating to the environment for 1 week, the mice were classified into test sample group and control group (1 mouse per cage). 50 mg/kg of streptozotocin (S0130, STZ, Sigma-Aldrich USA) was intraperitoneally administrated to test sample group for five consecutive days and 0.05 M sodium citrate buffer (pH 4.5, IBS-BC0036, Intron, Korea) was intraperitoneally administrated to negative control group for five consecutive days.

3 weeks after the administration, the fasting blood sugar level of mouse tail was determined by collecting blood sample at every four hours and the mice showing more than 350 mg/dl of fasting blood sugar were selected only in the experiment.

50 mg/kg of streptozotocin (S0130, STZ, Sigma-Aldrich USA) was intraperitoneally administrated to test sample group for five consecutive days (See FIG. 2) and 0.05 M sodium citrate buffer (pH 4.5, IBS-BC0036, Intron, Korea) was intraperitoneally administrated to negative control group for five consecutive days. The level of fasting blood sugar for 4 hours and weight of mice were determined at every 3 weeks and 5 weeks.

As can be seen in Table 6 and Table 7, it has been confirmed that the weight of STZ-diabetes induced mice was reduced and the fasting blood sugar level of those was increased. The selected mice of which fasting blood sugar level more than 350 mg/dl were regarded as diabetes-model group (Long M, Rojo de la Vega M, Wen Q, Bharara M, Jiang T, Zhang R, Zhou S, Wong P K, Wondrak G T, Zheng H, Zhang D D (2016) An Essential Role of NRF2 in Diabetic Wound Healing. *Diabetes*. 65:780-793)

TABLE 6

The change on the weight of STZ-induced diabetes-model mice

|  | weight (g) | | | SD* | | |
|---|---|---|---|---|---|---|
|  | Day 0 | Day 3 | Day 5 | Day 0 | Day 3 | Day 5 |
| Con | 23.16 | 25.94 | 26.72 | 0.93 | 1.20 | 0.29 |
| STZ + DIW | 23.52 | 21.92 | 22.06 | 0.74 | 0.70 | 1.04 |
| STZ + NP | 23.82 | 21.6 | 21.16 | 1.09 | 0.74 | 1.15 |

*SD: Standard deviation

TABLE 7

The change on the fasting blood sugar of STZ-induced diabetes-model mice

|  | Blood sugar level (mg/dL) | | | SD* | | |
|---|---|---|---|---|---|---|
|  | Day 0 | Day 3 | Day 5 | Day 0 | Day 3 | Day 5 |
| Con | 144.4 | 152 | 158.8 | 24.73 | 24.06 | 20.00 |
| STZ + DIW | 156.6 | 389.2 | 480.6 | 20.59 | 34.59 | 16.42 |
| STZ + NP | 151.4 | 437.2 | 491 | 20.09 | 25.83 | 39.53 |

*SD: Standard deviation sample group and 35 µl DIW was daily spread on the skin wound of negative control group.

The skin wound was photographed and imaged by digital camera (LD V20 digital camera) for 14 days and the size of skin wound was quantitatively determined by photoshop CS5 program (Adobe).

The healed rate of skin wound was calculated by dividing each sample by the size of the first wound according to following mathematical formula 1 as shown below.

$$\text{The healed rate of skin wound} = (\text{Day N}/\text{Day 0}) \times 100 \qquad \text{[Math. 1]}$$

4-3. Test Result (Skin Ulcer)

As can be seen in FIG. 3, the healing rate of diabetes-induced group was reduced comparing with that if negative control group treated with DIW while that of test-sample group was sharply increased comparing with those of diabetes-induced group as well as negative-control group.

After imaging the wound with a camera (LG V20 cell phone camera) to calculate the wound area, we calculated the number of pixels and compared them quantitatively. As can be seen in Table 8, the it has been confirmed that the inventive combined extract showed faster healing effect on skin ulcer area of the diabetic mouse comparing with negative control group from the 6th day after the injury of skin wound.

TABLE 8

Improving effect on skin ulcer area

|  | skin ulcer area (%) | | | SD | | |
|---|---|---|---|---|---|---|
|  | Con | STZ + DIW | STZ + NP | Con | STZ + DIW | STZ + NP |
| Day 0 | 100 | 100 | 100 | 0 | 0 | 0 |
| Day 3 | 60.84148 | 90.06944 | 78.4669 | 8.656211 | 7.466538 | 5.462093 |
| Day 6 | 36.87717 | 59.5353 | 36.926 | 9.241531 | 7.106927 | 7.088473 |
| Day 8 | 18.20702 | 48.83158 | 23.55075 | 3.185915 | 8.51045 | 9.839982 |
| Day 10 | 12.76884 | 22.70063 | 13.31474 | 4.074972 | 6.651348 | 5.455846 |
| Day 12 | 5.428536 | 12.01001 | 9.053564 | 3.243584 | 4.522714 | 2.306299 |
| Day 14 | 2.669485 | 10.03802 | 5.296044 | 2.512582 | 3.14416 | 0.822959 |

*SD: Standard deviation

4-2. Experimental Method (Treating Effect on Chronic Ulcer)

To confirm the treating effect of inventive extract on chronic ulcer, the animal model test using by Diabetes-induced mice prepared in above step 4-1, was performed according to the method disclosed in the reference (Long M, Rojo de la Vega M, Wen Q, Bharara M, Jiang T, Zhang R, Zhou S, Wong P K, Wondrak G T, Zheng H, Zhang D D (2016) An Essential Role of NRF2 in Diabetic Wound Healing. *Diabetes*. 65:780-793)

8 weeks old C57BL male mice (230 g, Daehanbiolink Co. Ltd) were classified into (a) control group and (b) diabetes-induced mice group prepared in above step 4-1, and the mice were anesthetized with the intraperitoneal injection of 300 µl of Avertin (25 mg/mL T48402, Sigma-Aldrich, USA).

After confirmation of anesthesia, the back-hair of mice was removed with using an electric razor (327/808, RIKEI, Taiwan) and the entire layer of skin on the back of a 5 mm circle was cut out with a 5 mm biopsy punch (BP-50F, Kai Industries, USA) and surgical scissors (PF-24.10, Professional, Pakistan). 35 µl of inventive extract dissolved in DIW (10 mg/mL) was daily spread on the skin wound of test

Experimental Example 5. Recovering Effect on Skin Wound (In Vivo)

To confirm the recovering effect of inventive extract on skin wound, the histological differences between the test sample group and control group using by diabetes-induced mice prepared in above step 4-1, was performed based on the test result of step 4-3 according to the method disclosed in the reference (Long M, Rojo de la Vega M, Wen Q, Bharara M, Jiang T, Zhang R, Zhou S, Wong P K, Wondrak G T, Zheng H, Zhang D D (2016) An Essential Role of NRF2 in Diabetic Wound Healing. *Diabetes*. 65:780-793)

5-1. Experimental Method (Recovering Effect on Skin Wound)

8 weeks old C57BL male mice (230 g, Daehanbiolink Co. Ltd) were classified into (a) control group and (b) diabetes-induced mice group prepared in above step 4-1, and the mice were anesthetized with the intraperitoneal injection of 300 µl of Avertin (25 mg/mL T48402, Sigma-Aldrich, USA).

After confirmation of anesthesia, the back-hair of mice was removed with using an electric razor (327/808, RIKEI, Taiwan) and the entire layer of skin on the back of a 5 mm circle was cut out with a 5 mm biopsy punch (BP-50F, Kai Industries, USA) and surgical scissors (PF-24.10, Professional, Pakistan). 35 μl of inventive extract dissolved in DIW (10 mg/mL) was daily spread on the skin wound of test sample group and 35 μl DIW was daily spread on the skin wound of negative control group.

At 7th day of skin injury, the wound tissue was isolated by surgery and the isolated wound tissue was dipped into 4% paraformaldehyde solution (158127, Sigma, USA) to be fixed with stirring in the shaker (4° C.) for overnight.

The next day, the wound tissue was put into a vial containing PBS at room temperature (RT), and washed five times every 15 minutes.

Afterwards, the wound tissue was placed in ethanol solution in the order of 25%, 50%, 75%, 95%, and 100%, and placed on the shaker (SHK039, Jeong Biotech, Korea) for 30 minutes to undergo dehydration.

The dehydrated skin tissue was transferred to the xylene solution (1330-20-7, DUKSAN, Korea) and left on the vacuum cleaner for two hours to allow xylene to permeate the tissue.

After confirming the transparency of the tissue, the tissue contained in xylene was transferred to an oven (oven, 300, CHICAGO SURGICAL & ELECTRICAL CO., USA) at 55° C. and washed five times in a paraffin solution (8042-47-5, Merck Millipore, Germany). The last paraffin solution was added thereto and kept at 55° C. overnight in the oven. The next day, the tissue was embedded in the paraffin, hardened for an hour at room temperature (RT), and placed at 4° C. for a day. Using microtomes (820, AO AMERICAN OPTICAL, USA), the paraffin-embedded tissue was sectioned to a thickness of 5 μm and these paraffin sections were placed on the slide glass. The remaining paraffin was removed with xylene and the tissue was hydrated in order of 100%, 95%, 75%, 50%, and 25% ethanol solutions. The tissue was then stained with hematoxylin and eosin (H&E) and photographed and analyzed using the EVOS XL Core microscope (USA, 40 times magnitude).

4-3. Test Result (Skin Wound)

As can be seen in FIG. 4, interestingly, the granulation tissue, which was not observed in the control group, was observed in the test sample group treated with inventive combined extract. The granulation tissue consists of numerous new blood vessels, fibroblasts, and cells such as growth factors, formed during the proliferation of wound healing (Grotendorst G R, Martin G R, Pencev D, Sodek J, Harvey A K (1985) Stimulation of granulation tissue formation by platelet-derived growth factor in normal and diabetic rats. *The journal of clinical investigation.* 76:2323-2329.).

The frequency of observation of granulation tissue in the test sample group was five times higher than that of control group (See Table 9).

TABLE 9

| recovering effect on skin wound | |
|---|---|
| | Formation of granulation tissue (%) |
| STZ + DIW | 14 |
| STZ + NP | 71.4 |

Experimental Example 6. Inhibitory Effect on the Expression of Pro-Inflammatory Cytokines Involved in Growth Factor (In Vivo)

In order to determine the inhibitory effect of inventive extract on the expression of pro-inflammatory cytokines involved in growth factor, following inhibition test on cytokine expression using test animal was performed according to the procedure disclosed in the literature (Long M, Rojo de la Vega M, Wen Q, Bharara M. Jiang T, Zhang R, Zhou S, Wong P K, Wondrak G T, Zheng H, Zhang D D (2016) An Essential Role of NRF2 in Diabetic Wound Healing. *Diabetes.* 65:780-793.)

There has been reported that the increase in abnormal expression of MMP-9 and the decrease in expression of growth factors (PDGF. VEGF, etc.) has been found in chronic wounds (Trengove N J, Bielefeldt-Ohmann H, Stacey M C (2001) Mitogenic activity and cytokine levels in non-healing and healing chronic leg ulcers. *Wound Repair and Regeneration.* 8:13-25.; Armstrong D G, Jude E B (2002) The Role of Matrix Metalloproteinases in Wound Healing. *Journal of the American Podiatric Medical Association.* 92:12-18.).

In particular, the growth factors promote the formation of granulation tissues to mediate wound healing (Leoni G, Neumann P A, Sumagin R, Denning T L, Nusrat A (2015) Wound repair: role of immune-epithelial interactions. *Mucosal Immunology.* 8:959-968.).

Accordingly, the inhibiting effect of the inventive combined extract on the gene expression was determined by following quantitative RT-PCR and Western blot analysis.

6-1. RNA Extraction and Quantitative RT-PCR

A wound skin tissue of the mouse was obtained using surgical scissors (PF-24.10, Professional, Pakistan) at a distance of 3 mm from both sides of the wound at 7th day. The skin tissue was frozen in liquid nitrogen (Dongas, Korea) to extract total RNA. Tri-RNA regent (FATR001, Favorgen, Taiwan) was added to the frozen skin tissue and crushed using head (D1031-05, Bedbug, USA).

After adding and mixing with 0.2 mL of chloroform (67-66-3, JUNSEI, Japan) sufficiently, centrifugation was performed using a centrifuge (5415R, Eppendorf, Germany) for 10 minutes at 12,000 rpm and 4° C.

After transferring only the upper layer solution to the new microcentrifuge tube (S044378, SARSTEDT AG5CO.KG, Germany), 0.4 mL of isopropanol was added and mixed together and centrifuged using centrifuges (5415R, Eppendorf, Germany) for 20 minutes at 12,000 rpm and 4° C. to precipitate RNA product.

After washing RNA sediment with 75% ethanol, centrifugation was performed for 10 minutes at 12,000 rpm and 4° C. RNA was dissolved in nuclease free water (S002, Enzynomics, Korea).

Recombinant DNase I (M0595, Enzynomics, Korea) was added thereto and left on incubator at 37° C. (incubator, BF-150N, Biofree, Korea) for 30 mins. 8 M Lithium chloride (L9650, Sigma, USA) was added thereto and left alone at −20° C. overnight.

The next day, after centrifuging at 12,000 rpm and 4° C. for 20 minutes, the RNA precipitate was washed with 75% ethanol and then centrifuged at 12,000 rpm and 4° C. for 10 minutes. The RNA was dissolved into nuclease free water (S002, Enzynomics, Korea) and quantified.

cDNA was synthesized from the total RNA template using PrimeScript™RT Master Mix (RR036A, Takara, Japan), and performs qRT-PCR was performed by using the synthesized cDNA by SYBR green kit (RT500M, Enzynomics, Korea) and Stratagene Mx3000p (MX3000p, Agilent, USA).

The resulting analysis was done by the following mathematical formula 2 to obtain a Ct value of 18S by subtracting the Ct value from the cycle threshold (Ct) value of the desired gene, and $(1/2)^{\wedge}$calibrated ct value. The sequence list of used primers is shown in Table 10.

$$\text{Relative Quantity} = (1/2)^{\wedge}(\text{Desired Gene Ct-18S Ct}) \qquad \text{[Math. 2]}$$

TABLE 10

Primer sequences used for quantitative PCR.

| gene* | direction | sequence | seq. no. |
|---|---|---|---|
| MMP-9 | forward | 5'-TGT CTG GAG ATT CGA CCT GAA GTC-3' | 9 |
| | reverse | 5'-TGA GTT CCA GGG CAC ACC A-3' | 10 |
| PDGF-A | forward | 5'-TGG CTC GAA GTC AGA TCC ACA-3' | 11 |
| | reverse | 5'-TTC TCG GGC ACA TGG TTA ATG-3' | 12 |
| VEGF-A | forward | 5'-ATT GAG ACC CTG GTG GAC ATC T-3' | 13 |
| | reverse | 5'-TGC ATG GTG ATG TTG CTC TCT G-3' | 14 |
| 18S | forward | 5'-AGT CCC TGC CCT TTG TAC ACA-3' | 15 |
| | reverse | 5'-CGA TCC GAG GGC CTC ACT A-3' | 16 |

*abbreviation- MMP (matrix metalloproteinase)); PDGF (Platelet-derived growth factor)/VEGF-A (Vascular endothelial growth factor)

6-2. Western Blot Analysis

A wound skin tissue of the mouse was obtained using surgical scissors (PF-24.10, Professional, Pakistan) at a distance of 3 mm from both sides of the wound at 7th day. The skin tissue was added to the PBS solution and washed overnight in the shaker at 4° C. The skin tissue was placed in RIPA buffer (self-prepared, 0.1% SDS, 0.5% sodium deoxycholate, 1% Triton X-100, 2 mM EDTA, 50 mM Tris-HCl (pH 8.0), 150 mM NaCl), and incubated in ice for 30 minutes.

After adding 5× sample buffer (self-prepared, 1 M Tris-HCl (pH 6.8), 50% glycerol, 10% SDS, 2-mercaptoethanol, and 1% bromophenol blue) thereto, the tissue was boiled at 100° C. for 7 minutes and cooled down in Ice for three minutes to isolate proteins from SDS-PAGE gel. The primary antibodies against MMP-9 (Millipore, USA, AB19016), VEGF-A (abcam, UK, ab46154), PDGF-A (Santa cruz, USA, sc-9974), β-tubulin (Santa cruz, USA, sc-166729) were used in the experiment.

As can be seen in Table 11 showing reducing effect on MMP expression and increasing effect on growth factors of inventive combined extract at RNA level and protein level, it has been confirmed that the test sample group treated with the inventive extract, sharply inhibited the expressed level of various cytokine involved in skin ulcer as well as skin wound (MMP-9) of STZ-induced diabetes mice as well as promoting effect on growth factor (PDGF-A, VEGF-A) comparing with negative control group treated with distilled water (DIW)

Accordingly, it has been confirmed that the inventive combined extract prepared in Example has potent inhibitory effect on in skin ulcer as well as skin wound and promoting effect on growth factors playing an important role during skin proliferation stage.

TABLE 11

Inhibition effect on cytokine expression and promoting effect on growth factor

| | MMP9 | | | VEGF | | | PDGF | | |
|---|---|---|---|---|---|---|---|---|---|
| | Con | STZ + DIW | STZ + NP | Con | STZ + DIW | STZ + NP | Con | STZ + DIW | STZ + NP |
| Relatively expressed amount (fold) | 1.00 | 3.00 | 1.87 | 1.00 | 1.15 | 2.65 | 1.00 | 1.39 | 4.63 |
| SD | 0.16 | 0.32 | 0.14 | 0.18 | 0.53 | 0.34 | 0.40 | 0.32 | 1.44 |

*SD: Standard deviation

The skin tissue was cut into small pieces with scissor (PF-24.10, Professional, Pakistan), and crushed with a microtubule homogenizer (985370, DREMEL, and Mexico). The sliced skin tissue was centrifuged with a centrifuge (5415R, Eppendorf, Germany) for 10 minutes at 13,000 rpm and 4° C. and the supernatant was transferred.

In particular, PDGF is a recently developed as a protein treating agent of chronic ulcer and VEGF is a vascular growth factor. (DiGiovanni C W, Petricek J M. The evolution of rhPDGF-BB in musculoskeletal repair and its role in foot and ankle fusion surgery. Foot Ankle Clin. 2010; 15:621-640. DiGiovanni and Petricker, 2010; Shi R, Lian W, Han S, Cao C, Jin Y, Yuan Y, Zhao H, Li M. Nanospheremediated codelivery of VEGF-A and PDGF-B genes for accelerating diabetic foot ulcers healing in rats. Gene Ther. 2018; 25:425-438.).

Statistics Analysis

The average and standard error were calculated from the test results obtained from the experiment. The significance difference test was analyzed using t-test, and the significance level (P-value) was expressed as $P \leq 0.05 =$*, $P \leq 0.01 =$, and $P \leq 0.001 =$*.

MODE FOR THE INVENTION

Hereinafter, the formulating methods and kinds of excipients will be described, but the present invention is not limited to them. The representative preparation examples were described as follows.

Preparation of Skin Lotion
Extract of Example (WIN-1001X) 1.00%
Glycerol 3.00%
Ethanol 1.00%
Propylene glycol 0.10%
Flavour trace amount
Distilled water up to 100%

Skin preparation was prepared by dissolving the active components according to conventional lotion preparation method.

Preparation of Lotion
Extract of Example (WIN-1002X) 3.00%
L-ascorbic acid-2-magnesium phosphate 1.00%
Soluble collagen (1% solution) 1.00%
Sodium citric acid 0.10%
1,3-butylene glycol 3.00%
Distilled water up to 100%

Lotion preparation was prepared by dissolving the active components according to conventional lotion preparation method.

Preparation of Cream
Extract of Example (WIN-1003X) 3.00%
Polyethyleneglycomonosterate 2.00%
Monostearate glycerin 1.00%
Cetyl alcohol 4.00%
Squalene 6.00%
Tri 2-glycerly ethylhexanoate 6.00%
Sphingo-glycolipid 1.00%
1,3-butylene glycol 3.00%
Distilled water up to 100%

Cream preparation was prepared by dissolving the active components according to conventional cream preparation method.

Preparation of Pack
Extract of Example (WIN-1004X) 5.00%
Polyvinyl alcohol 13.00%
L-ascorbic acid-2-magnesium phosphate 1.00%
Lauroylhydroxyproline 1.00%
Soluble collagen (1% solution) 2.00%

1,3-butylene glycol 3.00%
Ethanol 5.00%
Distilled water up to 100%
Sugar 20 g
Fructose 20 g
Lemon flavor optimum amount
Distilled water 100 ml Pack preparation was prepared by dissolving the active components according to conventional pack preparation method.

Preparation of Beauty Solution
Extract of Example (WIN-1005X) 2.00%
Hydroxyethylene cellulose (2% solution) 12.00%
Xanthin gum (2% solution) 2.00%
1,3-butylene glycol 3.00%
Glycerin concentration 4.00%
Sodium hyaluronate 5.00%
Distilled water 100 ml Beauty solution preparation was prepared by dissolving the active components according to conventional beauty solution preparation method The invention being thus described as will be obvious that it may be varied in many ways. Such variations are not to be regarded as a departure from the spirit and scope of the present invention, and all such modifications as would be obvious to those skilled in art are intended to be included within the scope of the following claims.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

As described in the present invention, the present invention provides a topical composition and cosmetic composition comprising a combined herb extract of Longanae Arillus, Ligustici Tenuissimi Rhizoma and Polygalae radix, the present inventors demonstrated that the anti-ulcer effects of inventive combined composition are potent by accomplishing in vitro experiments such as inhibitory effect on cytokine expression (in vitro). (Experimental Example 1); Promoting effect on cell proliferation (in vitro). (Experimental Example 2); Recovering effect on cell wound (in vitro) (Experimental Example 3); as well as in vivo experiments such as the treating effect on chronic ulcer (in vivo) (Experimental Example 4); recovering effect on skin wound (in vivo) (Experimental Example 5); inhibitory effect on the expression of pro-inflammatory cytokines involved in growth factor (in vivo) (Experimental Example 6), therefore, it is confirmed that inventive combined extract is very useful in the alleviation or treatment of skin ulcer as a form of topical medicament or cosmetic composition.

The invention claimed is:

1. A topical pharmaceutical composition comprising a combined herb extract of *Longanae arillus, Ligustici tenuissimi rhizoma*, and *Polygalae radix* as active ingredients in therapeutically effective amounts to treat and alleviate skin ulcer, wherein said combined herb extract is in the form of an aqueous ethanolic extract;

wherein the extraction comprises extracting the herbs with 10-90% (v/v) ethanol in water; and wherein said combined herb extract consists of a mixture of each extract of *Longanae arillus, Ligustici tenuissimi rhizoma*, and *Polygalae radix* based on a dried weight (w/w) ratio respectively of (1-3):(1-3):(1-3).

2. The topical pharmaceutical composition according to claim 1, wherein said skin ulcer is selected from a decubitus ulcer or diabetic ulcer.

3. A method of treating or alleviating skin ulcer in a mammal comprising topically administering to said mammal an effective amount of the topical pharmaceutical composition of claim 1.

4. The method of treating or alleviating skin ulcer of claim 3, wherein the skin ulcer is selected from decubitus ulcer or diabetic ulcer.

\* \* \* \* \*

SEQUENCE LISTING

<160> NUMBER OF SEQ ID NOS: 16

<210> SEQ ID NO 1
<211> LENGTH: 19
<212> TYPE: DNA
<213> ORGANISM: Homo sapiens

<400> SEQUENCE: 1

-continued

```
agcccagaac actggtctc                                              19

<210> SEQ ID NO 2
<211> LENGTH: 21
<212> TYPE: DNA
<213> ORGANISM: Homo sapiens

<400> SEQUENCE: 2
actcaggatt tcaatggtgc c                                           21

<210> SEQ ID NO 3
<211> LENGTH: 23
<212> TYPE: DNA
<213> ORGANISM: Homo sapiens

<400> SEQUENCE: 3
tatgagtggg accaaaagta ccg                                         23

<210> SEQ ID NO 4
<211> LENGTH: 22
<212> TYPE: DNA
<213> ORGANISM: Homo sapiens

<400> SEQUENCE: 4
gggattgaag gttaggctct gg                                          22

<210> SEQ ID NO 5
<211> LENGTH: 22
<212> TYPE: DNA
<213> ORGANISM: Homo sapiens

<400> SEQUENCE: 5
tcctgaacct gagtagagac ac                                          22

<210> SEQ ID NO 6
<211> LENGTH: 19
<212> TYPE: DNA
<213> ORGANISM: Homo sapiens

<400> SEQUENCE: 6
tgctgcttgt agtggctgg                                              19

<210> SEQ ID NO 7
<211> LENGTH: 20
<212> TYPE: DNA
<213> ORGANISM: Homo sapiens

<400> SEQUENCE: 7
ctccagggac aggatatgga                                             20

<210> SEQ ID NO 8
<211> LENGTH: 20
<212> TYPE: DNA
<213> ORGANISM: Homo sapiens

<400> SEQUENCE: 8
tctttcaaca cgcaggacag                                             20

<210> SEQ ID NO 9
<211> LENGTH: 24
<212> TYPE: DNA
<213> ORGANISM: Mus musculus
```

-continued

```
<400> SEQUENCE: 9
tgtctggaga ttcgacctga agtc                                        24

<210> SEQ ID NO 10
<211> LENGTH: 19
<212> TYPE: DNA
<213> ORGANISM: Mus musculus

<400> SEQUENCE: 10
tgagttccag ggcacacca                                              19

<210> SEQ ID NO 11
<211> LENGTH: 21
<212> TYPE: DNA
<213> ORGANISM: Mus musculus

<400> SEQUENCE: 11
tggctcgaag tcagatccac a                                           21

<210> SEQ ID NO 12
<211> LENGTH: 21
<212> TYPE: DNA
<213> ORGANISM: Mus musculus

<400> SEQUENCE: 12
ttctcgggca catggttaat g                                           21

<210> SEQ ID NO 13
<211> LENGTH: 22
<212> TYPE: DNA
<213> ORGANISM: Mus musculus

<400> SEQUENCE: 13
attgagaccc tggtggacat ct                                          22

<210> SEQ ID NO 14
<211> LENGTH: 22
<212> TYPE: DNA
<213> ORGANISM: Mus musculus

<400> SEQUENCE: 14
tgcatggtga tgttgctctc tg                                          22

<210> SEQ ID NO 15
<211> LENGTH: 21
<212> TYPE: DNA
<213> ORGANISM: Mus musculus

<400> SEQUENCE: 15
agtccctgcc ctttgtacac a                                           21

<210> SEQ ID NO 16
<211> LENGTH: 19
<212> TYPE: DNA
<213> ORGANISM: Mus musculus

<400> SEQUENCE: 16
cgatccgagg gcctcacta                                              19
```